United States Patent
Tillotson

(10) Patent No.: US 8,345,115 B2
(45) Date of Patent: Jan. 1, 2013

(54) VISUAL OCCULTATION TO MEASURE REFRACTIVITY PROFILE

(75) Inventor: Brian J. Tillotson, Kent, WA (US)

(73) Assignee: The Boeing Company, Chicago, IL (US)

( * ) Notice: Subject to any disclaimer, the term of this patent is extended or adjusted under 35 U.S.C. 154(b) by 599 days.

(21) Appl. No.: 12/533,807

(22) Filed: Jul. 31, 2009

(65) Prior Publication Data

US 2011/0025868 A1  Feb. 3, 2011

(51) Int. Cl.
H04N 5/228 (2006.01)
(52) U.S. Cl. .................................... 348/222.1
(58) Field of Classification Search ............... 348/222.1
See application file for complete search history.

(56) References Cited

U.S. PATENT DOCUMENTS

| | | |
|---|---|---|
| 6,903,752 B2 | 6/2005 | Ebersole et al. |
| 7,343,793 B2 | 3/2008 | Tillotson et al. |
| 7,365,674 B2 | 4/2008 | Tillotson et al. |
| 7,530,266 B2 | 5/2009 | Tillotson et al. |
| 7,925,052 B2 * | 4/2011 | Bar-Sagi ................ 382/107 |
| 2006/0121893 A1 * | 6/2006 | Tillotson et al. ......... 455/431 |
| 2009/0009393 A1 | 1/2009 | Tillotson et al. |
| 2009/0143988 A1 | 6/2009 | Tillotson |
| 2009/0290760 A1 * | 11/2009 | Bar-Sagi ................ 382/107 |
| 2010/0192709 A1 * | 8/2010 | Wilcox et al. ............ 73/865.6 |
| 2011/0085698 A1 * | 4/2011 | Tillotson ................ 382/103 |

FOREIGN PATENT DOCUMENTS

| | | |
|---|---|---|
| RU | 1464676 | 7/1993 |
| RU | 1438419 | 2/1994 |
| SU | 1610452 | 11/1990 |
| SU | 1603985 | 7/1992 |
| SU | 1448908 | 10/1992 |

OTHER PUBLICATIONS

GB, Combined Search and Examination Report, Application No. GB1012593.8 (Oct. 06, 2010).

* cited by examiner

Primary Examiner — James Hannett
(74) Attorney, Agent, or Firm — Robert B. Parker

(57) ABSTRACT

Presented is a system and method for measuring the refractivity profile of a parcel of atmosphere comprising an image capturing device for capturing an image of a visual feature, such as a topographic feature like the horizon, combined with a lens having focal length adapted to focus an image onto image capturing device such that the combination of the lens and the image capturing device are adapted to resolve at least 100 microradians of angle, and an image processor adapted to compare a detected position of the visual feature in the image to the expected position of the visual feature. The system uses the difference between the detected position and the expected position to detect the change in arrival angle caused by atmospheric refraction of light from the visual feature as it passes through the atmosphere.

13 Claims, 7 Drawing Sheets

VIEW 1

VIEW 2

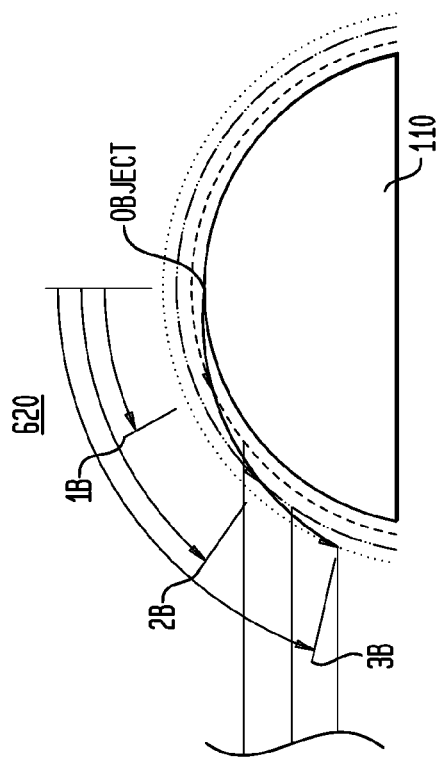
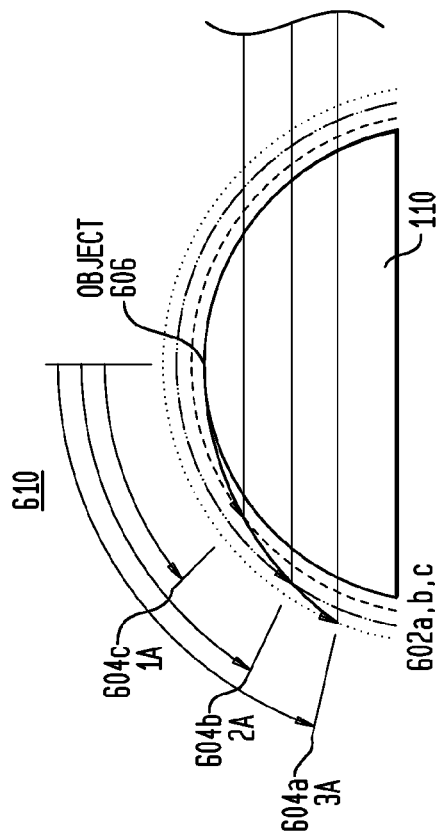

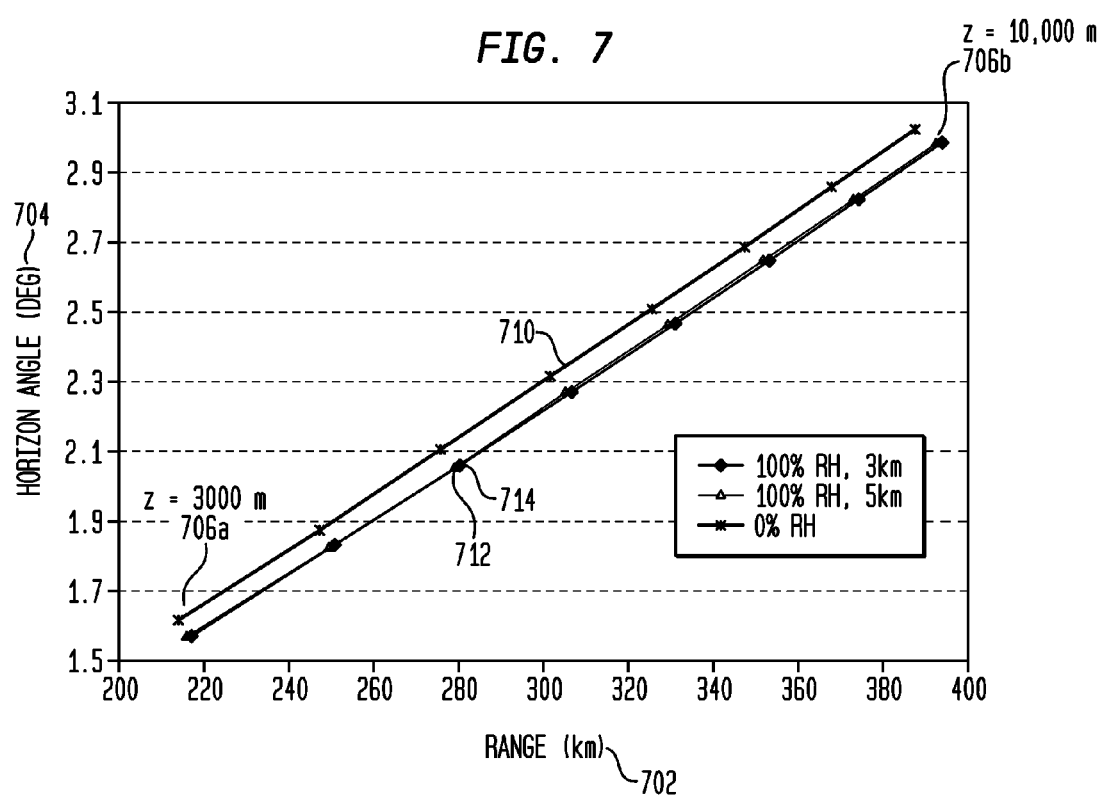

VISUAL OCCULTATION TO MEASURE REFRACTIVITY PROFILE

FIELD

Embodiments of the subject matter described herein relate generally to a system and method to estimate temperature and humidity levels in the atmosphere, and in particular to using a camera-based system on an airborne mobile platform to develop a refractivity profile of the atmosphere.

BACKGROUND

Measuring atmospheric conditions such as temperature and humidity allows aircraft and airborne vehicles to make flight adjustments to achieve a desired level of performance and avoid undesirable flying conditions. In addition, measuring the present state of atmospheric conditions is necessary to forecast future atmospheric events such as storms. Measuring the temperature and humidity of the atmosphere can be performed to varying degrees using ground-base instrumentation, by sensors carried aloft in balloons or other airborne vehicles, by sensors in aircraft as they pass through a region of atmosphere, and by using predictive modeling based on past measurements.

However, over oceans and in underdeveloped regions of the world, ground-based instrumentation and dedicated sensor equipment like weather balloons either do not exist or it may be economically impractical to cover an area with sufficient sensors to provide the desired level of accuracy. Additionally, aircraft may pass through an area too infrequently to provide current conditions for other later aircraft. And dynamic atmospheric conditions generally make modeling grow less precise over time, and although good for approximating general conditions for regional conditions, modeling can be inaccurate at finer granularities. Sensors, and especially fixed instrumentation, are limited to surveying portions of the atmosphere proximate to the sensor apparatus at the time the sensor measurements were made. A moving aircraft or airborne vehicle may travel through multiple overlapping zones of coverage and areas without coverage during a flight.

SUMMARY

Presented is a method and system for measuring the temperature and humidity of the atmosphere. The method and system detects small deviations in a visual scene that are caused by changes in the refractivity of the atmosphere, and measures the characteristics of these deviations to estimate the temperature and humidity and develop refractivity profiles of the atmosphere. These refractivity profiles can be used to improve atmospheric models, for example models of water vapor, and thereby improve weather forecasts.

The system and method offers remote measurements of meteorological variables with lower certification cost and faster certification schedule, lower unit cost, and lower weight compared to other methods such as aircraft-based GPS occultation. Further, the system and method provides coverage over ocean regions beyond sight of land.

The features, functions, and advantages discussed can be achieved independently in various embodiments of the present invention or may be combined in yet other embodiments further details of which can be seen with reference to the following description and drawings.

BRIEF DESCRIPTION OF THE DRAWINGS

The accompanying figures depict various embodiments of the system and method of visual occultation to measure refractivity profiles. A brief description of each figure is provided below. Elements with the same reference number in each figure indicated identical or functionally similar elements. Additionally, the left-most digit(s) of a reference number indicate the drawing in which the reference number first appears.

FIG. 6 is a diagram illustrating the use of refractivity profiles of overlapping atmospheric regions taken at different altitudes in order to derive a refractivity profile that is correlated with altitude;

FIG. 7 is a graph of the angular changes to the horizon as imaged at the aircraft over a range of distances to the horizon for three sample sets, one set of data points for the angle to the horizon with no refraction by the intervening atmosphere, one set of data points for refraction caused by humidity varying from 0% to 100% in a sinusoidal fashion with a 5 km half-wavelength, and one set of data points for refraction caused by humidity varying from 0% to 100% in a sinusoidal fashion with a 3 km half-wavelength;

DETAILED DESCRIPTION

The following detailed description is merely illustrative in nature and is not intended to limit the embodiments of the invention or the application and uses of such embodiments. Furthermore, there is no intention to be bound by any expressed or implied theory presented in the preceding technical field, background, brief summary or the following detailed description.

System Components and Operation

Figure 1:
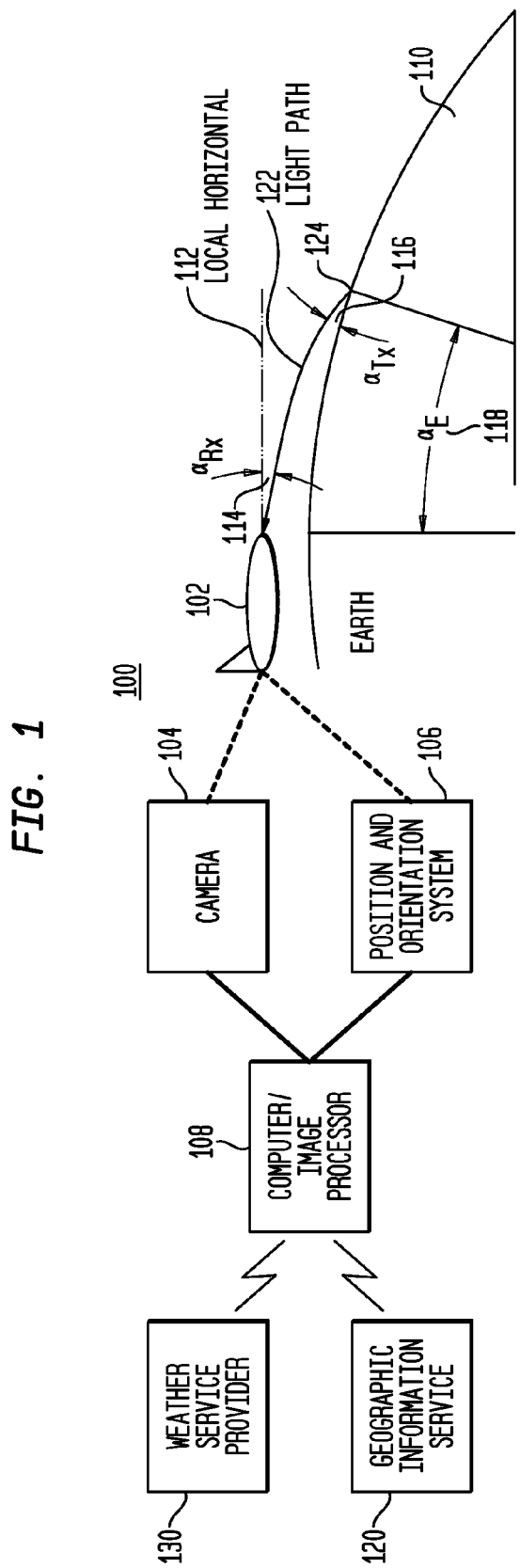
FIG. 1 is a diagram of an aircraft in flight above the earth, and the relationship of the horizontal orientation of the aircraft in relation to the received arrival angle of light and the departure angle of light from a topographical feature such as the horizon.

Referring now to FIG. 1, a refractivity profiling system 100 is shown. The refractivity profiling system 100 obtains refractivity information to predict atmospheric conditions in a parcel of atmosphere. The refractivity profiling system uses visual occultation to measure refractivity profiles of parcels of atmosphere. The refractivity profiles can be used to improve atmospheric models, for example models of water vapor, and thereby improve weather forecasts.

The refractivity profiling system 100 comprises an airborne platform, for example an aircraft 102 flying in the atmosphere above the earth 110, a camera 104, a position and orientation system 106, and a computer 108. In embodiments, the airborne platform is a commercial aircraft, a military aircraft, a radiosonde or weather balloon, or any other stationary or mobile platform positioned with a view of the surrounding atmosphere.

One or more cameras 104 are mounted on or to the aircraft 102, and a computer 108 for analyzing images from the cameras 104. The computer 108 can be any suitable computing platform capable of manipulating digital image data, including but not limited to a PC, workstation, a customized circuit board, or an image processor. The camera 104 is linked to the computer 108 that receives the image from the camera 104. In an embodiment, the camera 104 uses a telephoto lens. In operation, the camera 104 is pointed approximately at the horizon 124, or an feature having sufficient known detail, and a series of images or video is delivered to the computer 108. The camera 104 outputs digitized data of the image to the computer 108. In another embodiment, the computer 108 digitizes an analog input from the camera 104 into digital images using a digital frame grabber.

The image from the camera 104 is analyzed to detect small changes in the refractive index of air. Light returning to the camera 104 from the horizon 124 passes through a parcel of atmosphere and is refracted along light path 122. The change in refraction is due to the density and composition of air in the atmosphere, for example due to differences in humidity levels, temperatures, and pressures. As a result of the changes in refraction, the horizon 124 will appear shifted spatially. The refractive index of a parcel of air is given by an empirical formula shown in Eqn. 1. In this formula, N is refractivity (equal to the index of refraction, n, times $10^6$), T is the temperature in Kelvin, $p_d$ is the partial pressure of dry air, $p_v$ is the partial pressure of water vapor, $Z_d$ is the inverse compressibility factor for dry air and $Z_w$ is the inverse compressibility factor for wet air. The constants $k_1$, $k_2$ and $k_3$ are empirically determined.

$$N = k_1\left(\frac{p_d}{T}\right)Z_d^{-1} + \left[k_2\left(\frac{p_v}{T}\right) + k_3\left(\frac{p_v}{T^2}\right)\right]Z_w^{-1} \quad (1)$$

Weather-induced deviations in the refractive bending of light can be on the order of 100 microradians or less, which may be too small to be detected accurately by many cameras 104 using normal snapshot lenses. To increase accuracy and provide a finer level of granularity, the camera 104 in the refractivity profiling system 100 uses a telephoto lens having a long focal length that magnifies the image and provides a suitable resolution for imaging by the camera 104. In an embodiment, the telephoto lens and the pixel resolution of the image capturing element, for example a CCD chip or charge coupled device, are adapted to resolve at least 100 microradians of angle. In another embodiment, the system is adapted to have a minimum resolving capability of between 10 microradians and 100 microradians of angle. For example, a telephoto lens having a 1-meter focal length can resolve approximately $10^{-5}$ radians when coupled with a one $cm^3$ CCD chip having one micron pixels arranged in a 1000×1000 pixel matrix. In one embodiment, the telephoto lens is a zoom lens, capable of adjusting the magnification and therefore allowing the system operator to selectively trade off measurement accuracy for a wider field of view.

In an embodiment, the camera 104 includes a CCD having a very fine pitch, or a similar image capturing means, which is used to gather an image, either alone or in combination with a telephoto lens. To maximize the resolution, the CCD is a black and white CCD. Color CCDs generally use tiny filters arranged in a pattern over the CCD elements, which can cause unwanted image artifacts such as color changes near sharp edges of object depending upon how the light falls onto the CCD chip. Edge artifacts are unwanted image distortions that have the potential of being misinterpreted by the computer. In other embodiments, the system uses a 3-CCD camera 104 that divides the image into three different CCDs, for example using birefringent materials, and therefore does not induce unwanted edge artifacts.

In embodiments, the camera 104 is a digital frame camera, a video camera, a high-resolution CCD camera, or an HD camcorder. In embodiments, to enhance the image depth and dynamic range of the captured image, the camera 104 selectively uses filters, such as a polarization filter, a neutral density filter, or a red filter to avoid backscattered blue light. In embodiments, the camera 104 additionally is an infrared camera or selectively uses an image intensifier, such as a night vision tube, allowing the refractivity profiling system 100 to perform better in low light situations such as dusk or night time. In embodiments, the camera 104 is an image capturing device using a CCD, an analog sensor, a linear sensor such as a linear sensor array, or any other photosensitive sensor capable of determining fine pitch in a visual scene.

In an embodiment, the camera 104 is mounted on a rotatable swivel mount that allows the camera 104 to be rotated to view different portions of the sky. In an embodiment, the camera 104 is mounted on a multi-axis gimbal, allowing it to be angularly rotated in any direction. In these embodiments, the camera 104 may be rotated or oriented in order to scan a larger area. The output from the camera 104 is synchronized with an output from a rotational encoder or other similar orientation identifying means to correlate images from the camera 104 with the orientation of the camera 104.

The motion of the camera 104 is linked to the motion of the aircraft 102, for example through a position and orientation system 106 such as a navigation and control system, a GPS receiver, an inertial measurement unit or IMU, or any similar system or combination of systems. The IMU measures changes in camera orientation due to rotation or twisting of the aircraft 102 and can be used to maintain orientation of the camera 104 towards a desired point in the sky or on the horizon. In an embodiment, the camera 104 is substantially fixed and a rotatable mirror is used to change the direction of viewing of the camera 104. In an embodiment, the mirror is a first surface mirror for better clarity. In an embodiment, the camera 104 is mounted in a vibration reducing mount. In an embodiment, the camera 104 is gyroscopically stabilized.

Image Processing

Continuing to refer to FIG. 1, the computer 108 processes one or more images from the camera 104. The processing identifies visual features whose physical location is well known, e.g., the horizon 124 of the earth 110. Using the spatial position (in pixel rows and columns) of each visual feature on the focal plane, the pitch of pixels in the camera focal plane, and the focal length of the lens, the computer 108 measures the angular position of those visual features in the scene. It computes the difference between the measured angular position and the position each feature would have if the atmosphere did not refract as illustrated in light path 122. This difference is a function of the refractivity gradient at each point along the light path 122. Therefore, measuring the angular differences allows the refractivity profiling system 100 to estimate the refractivity profile for a parcel of atmosphere.

In embodiments, the refractivity profiling system 100 measures the arrival angle 114, $\alpha_{Rx}$, and the departure angle 116, $\alpha_{Tx}$, as a function of earth angle 118, $\alpha_E$. The arrival angle 114, $\alpha_{Rx}$, is measured relative to the local horizontal 112 at the camera 104 where it is received. The departure angle 116, $\alpha_{Tx}$, is measured relative to the local horizontal 112 at the features in the scene from which it is transmitted or reflected. Earth angle 118, $\alpha_E$, refers to the fraction of the circumference of the earth 110 that the light traverses along light path 122.

Measuring Arrival Angle

Figure 2A:
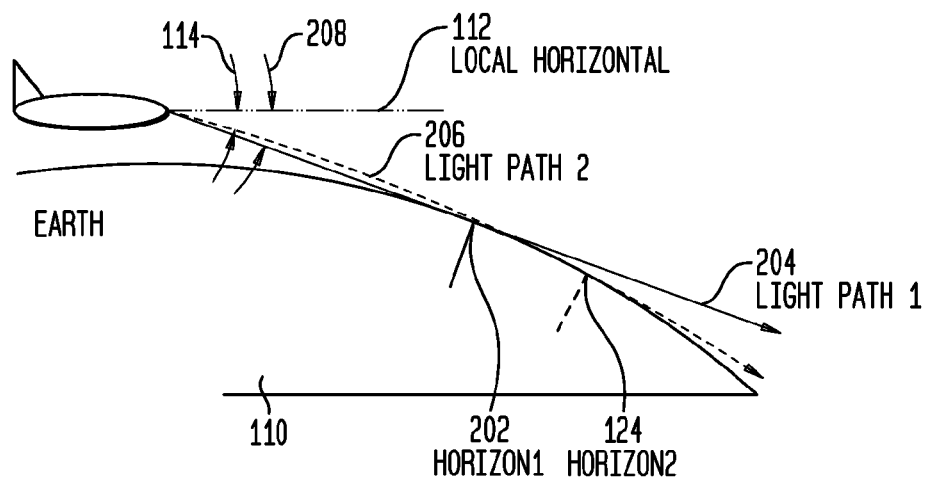
FIG. 2a is a diagram illustrating the change in the position of the horizon imaged by the aircraft due to refraction in the atmosphere.
Figure 2B:
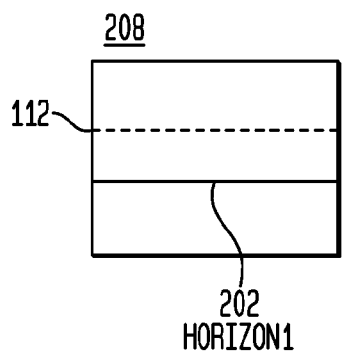
FIG. 2b is a diagram illustrating the imaged angular position of the horizon relative to the horizontal orientation of the aircraft when there is little or no refraction by the atmosphere.
Figure 2C:
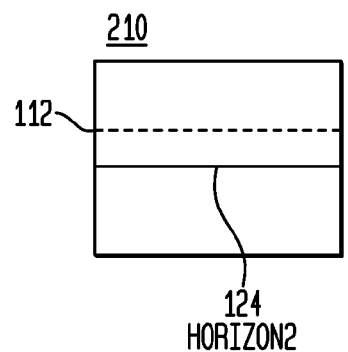
FIG. 2c is a diagram illustrating the imaged angular position of the horizon relative to the horizontal orientation of the aircraft when there is increased refraction by the atmosphere.

Referring now to FIGS. 2a, 2b, and 2c, the camera 104 in the aircraft 102 takes an image of the horizon 124, for example in the direction of travel of the aircraft 102. The computer 108 captures the images into an ordered matrix of pixels. For example, a 12 megapixel image having a 4:3 ratio comprises a rectangular image having 4000 pixels along one axis and 3000 pixels along a second axis.

Through means well known in the art, the computer 108 attached to the camera 104 uses data from the aircraft 102 position and orientation system 106, for example the navigation and control system, and computes the pixels in the image that are in the local horizontal 112 position (shown as a dot-dash line in FIG. 2a and as a dashed line in FIGS. 2b and 2c.) If the atmosphere did not refract the light at all, then light reaching the camera 104 from the un-refracted horizon 202 would travel the straight path labeled "Light path 1" 204. Since the atmosphere actually does refract light, light reaching the camera roughly follows the curved path labeled "Light path 2" 206. The result is that the horizon 124 appears higher in the actual image 210, FIG. 2c, than the un-refracted horizon 202 in a geometrically computed image 208, FIG. 2b. The computer 108 measures the observed arrival angle 114 of the horizon 124 in the image, compares it to the computed position and un-refracted arrival angle 208 of the un-refracted horizon 202 for the case where no atmospheric refraction occurs, and reports the difference. The angular difference between the true or computed geometric position and the observed position is dependent on the atmospheric refractivity profile. The path 122 of light in the atmosphere curves downward, as shown in FIG. 2a by "Light Path 2" 206, because the index of refraction for air is greater at lower altitudes. This gradient in the index of refraction bends the path 122 of any light not traveling vertically.

Measuring Departure Angle

To measure the departure angle 116, $\alpha_{Tx}$, one embodiment of the refractivity profiling system 100 further comprises a geographic information system, or GIS 120, having a database of visual terrain characteristics or other topographical information. In another embodiment, the refractivity profiling system 100 further comprises a communications link to a GIS 120.

Figure 3A:
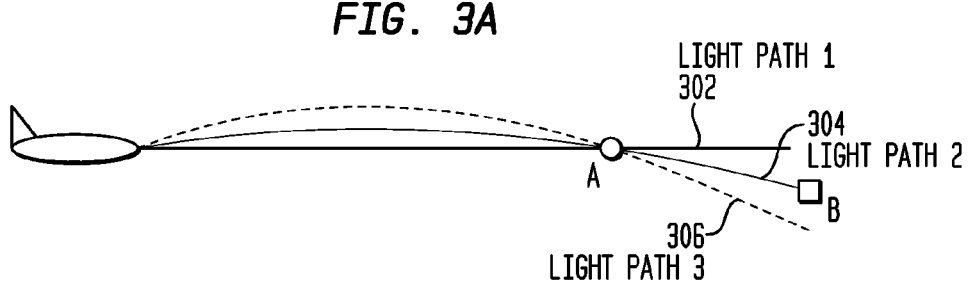
FIG. 3a is a diagram illustrating the change in the relative position of topographical features at different distances from the aircraft as imaged at the aircraft due to refraction in the atmosphere.
Figure 3B:
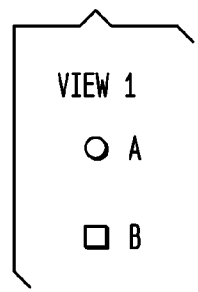
FIG. 3b is a diagram illustrating the true relative altitudes of two topographical features that are at different distances from the aircraft when there is little or no refraction by the atmosphere.
Figure 3C:
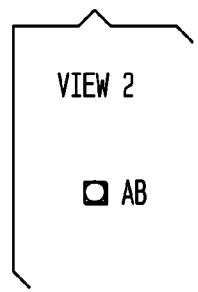
FIG. 3c is a diagram illustrating how the two topographical features are perceived as having the same altitude due to the refraction by the atmosphere and the difference in path lengths for light arriving at the aircraft from each of the features.
Figure 3D:
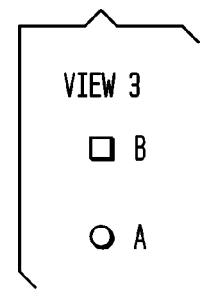
FIG. 3d is a diagram illustrating the perceived inversion of the two topographical features due to increased refraction in the atmosphere.

Referring now to FIGS. 3a, 3b, 3c and 3d, and FIGS. 4a, 4b, and 4c the departure angle 116, $\alpha_{Tx}$, can be measured by measuring inversion or compression of image features. FIG. 3a illustrates inversion, and shows the relative positions of two objects, A and B, as they would appear if viewed with three different levels of refractive bending. With "light path 1" 302 (no bending), object B appears below the line of sight to object A (FIG. 3b.) With "light path 2" 304 (moderate bending), object B appears directly aligned with object A (FIG. 3c.) With "light path 3" 306 (strong bending), object B appears above the line of sight to object A (FIG. 3d.)

Figure 4A:
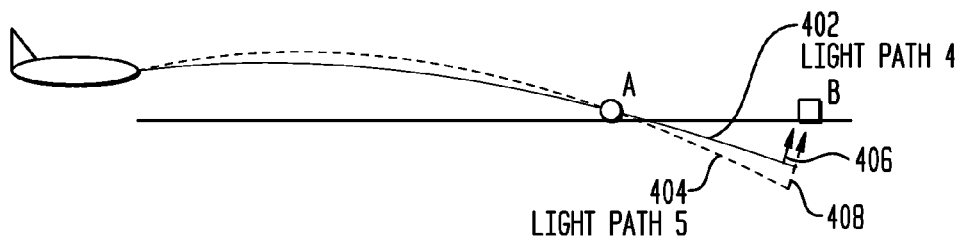
FIG. 4a is a diagram illustrating compression in the apparent distances between topographical features due to refraction in the atmosphere.
Figure 4B:
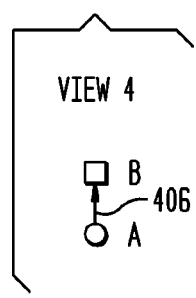
FIG. 4b is a diagram illustrating the true relative distances of two topographical features that are at different distances as would be imaged at the aircraft when there is little or no refraction by the atmosphere.
Figure 4C:
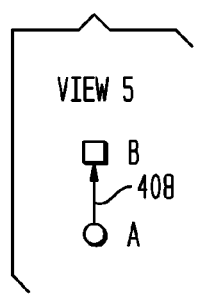
FIG. 4c is a diagram illustrating an increase in perceived distances between two topographical features as would be imaged when there is increased refraction by the intervening atmosphere.

FIG. 4a illustrates compression, which is more commonly observed than inversion, and shows two objects, A and B, that are lower than the airplane and at the same altitude, e.g., on the ground. With either moderate or strong refractive bending, object B appears above the line of sight to object A (FIGS. 4b and 4c.) However, the apparent vertical displacement 406, 408 of object B relative to object A in the image varies depending on the departure angle 116, $\alpha_{Tx}$ and determines whether the light takes path "light path 4" 402 or "light path 5" 404 to reach the airplane. Specifically, the vertical displacement 406, 408 equals the horizontal distance between the objects A and B, times the sine of the departure angle 116 relative to the local horizontal 112. Measuring this vertical displacement 406, 408 for objects whose positions are known reveals the departure angle 116, $\alpha_{Tx}$.

To measure the departure angle 116, $\alpha_{Tx}$, the refractivity profiling system 100 captures an image that includes at least two objects, A and B, whose physical locations are stored in a database connected to the computer 104, for example a GIS 120. Preferably, the objects have visually sharp features and are close enough together to appear within about 1/10 of a degree vertically from each other in the image. The computer 108 inputs the image, locates features associated with each object, computes the apparent vertical displacement 406, 408 between the objects A and B, divides that value by the horizontal distance between the objects, and computes the arc sine of the resulting quantity. This yields the departure angle 116. If object A and object B are not at exactly the same altitude, the processor accounts for the altitude difference between them when calculating the vertical displacement 406, 408 due to refraction.

In embodiments, the refractivity profiles are estimated using the arrival angle 114, $\alpha_{Rx}$, the departure angle 116, $\alpha_{Tx}$. In embodiments, an image is selected from a plurality of images, an image averaged from two or more images, or an image derived from two or more images.

In embodiments, the visual feature whose position is measured in the scene is an artificial object such as a building, or a vehicle whose location is known with sufficient precision. In embodiments, the camera is at a fixed location on the ground and measures the arrival angle of light from distant aircraft or objects whose positions are known.

Local Horizontal Confirmation

Figure 5A:
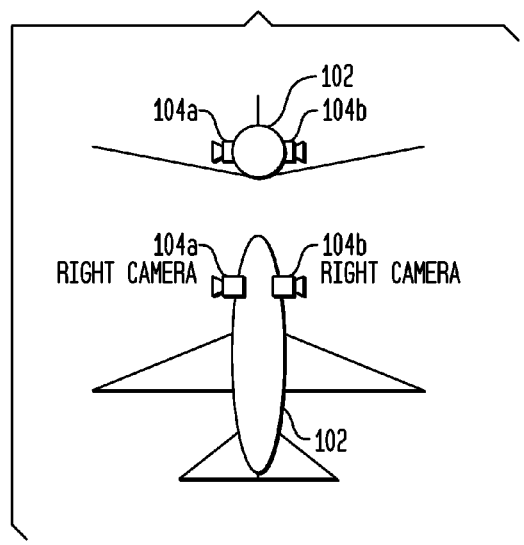
FIGS. 5a and 5b are diagrams illustrating a method of visually determining the orientation of the aircraft by using opposing camera views of the horizon in order to reduce the effects on the measurements caused by tilt or other changes in the orientation of the aircraft during operation.

Referring now to FIG. 5*a*, in an embodiment, the local horizontal 112 is confirmed using two or more opposite-facing cameras 104*a*, 104*b* to measure horizon arrival angle 114 $\alpha_{Rx}$ on both sides of an aircraft 104. This allows the refractivity profiling system 100 to cancel any aircraft 102 tilt bias. The horizon 124 is a particularly useful visual feature for measuring refractive bending angle or arrival angle 114, $\alpha_{Rx}$. The horizon 124 appears as a relatively straight, sharp line dividing the image into upper and lower regions with substantial contrast between the two regions. Refractive bending moves the dividing line between the regions as described above. The camera 104 and software in the computer 108 measure the displacement of this dividing line.

Figure 5B:
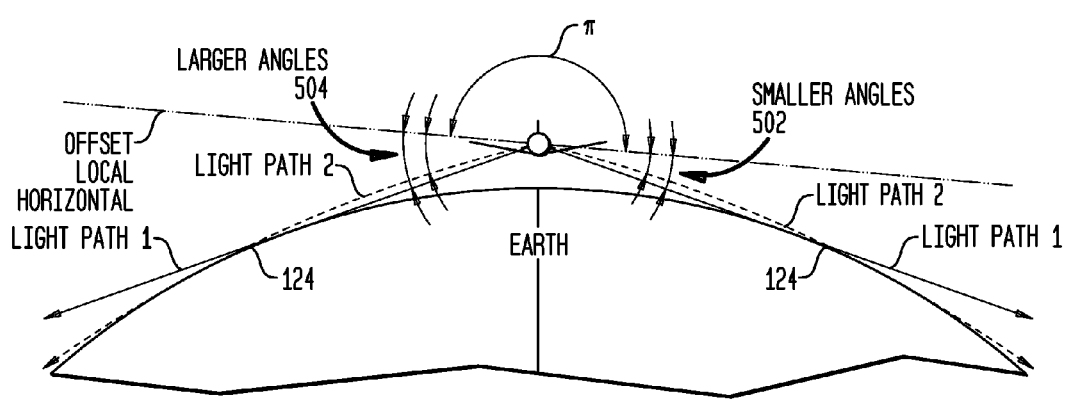

In FIG. 5*b*, the aircraft 102 is tilted slightly to the right, but its navigation system, or position and orientation system 106, incorrectly reports data indicating that the aircraft 102 is level. With a single camera 104, the estimated position of local horizontal 112 in the image would be incorrect by an amount equal to the tilt of the aircraft 102. With two cameras facing 180° (p radians) apart, a too-high horizon 502 in one image is matched by a too-low horizon 504 in the other. The computer 108 in this embodiment uses images from both cameras 104*a*, 104*b* to correct for the offset 506 to the local horizontal 112.

Altitude Correlation for Refractivity Profiling

Figure 8:
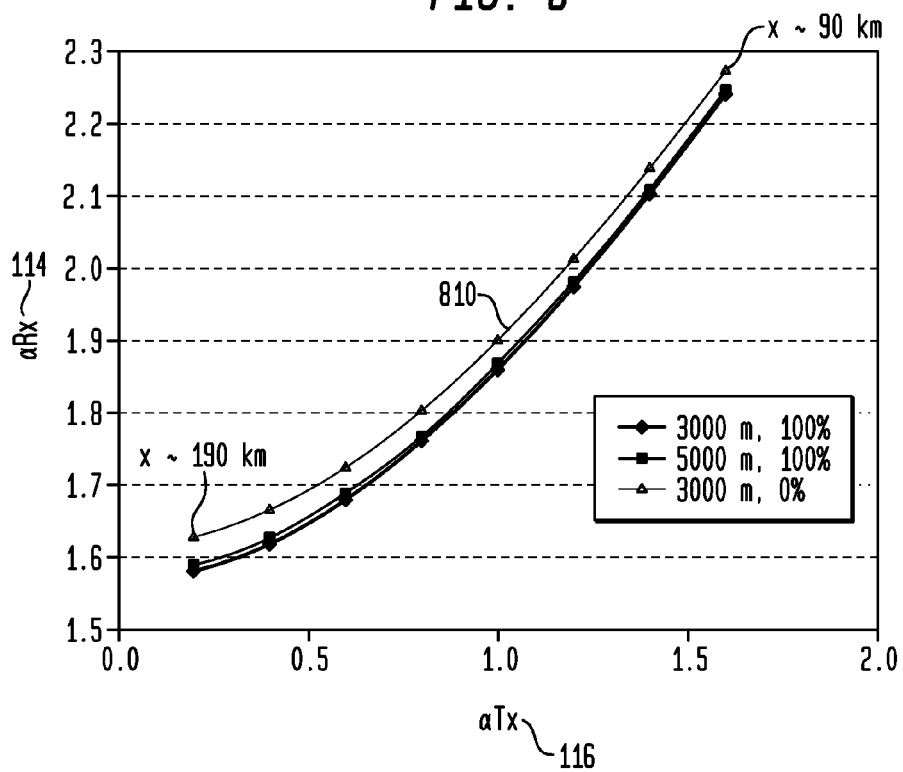
FIG. 8 is a graph of the departure angle and the arrival angle of the horizon as imaged at the aircraft for the same three sample sets as FIG. 7.
Figure 9:
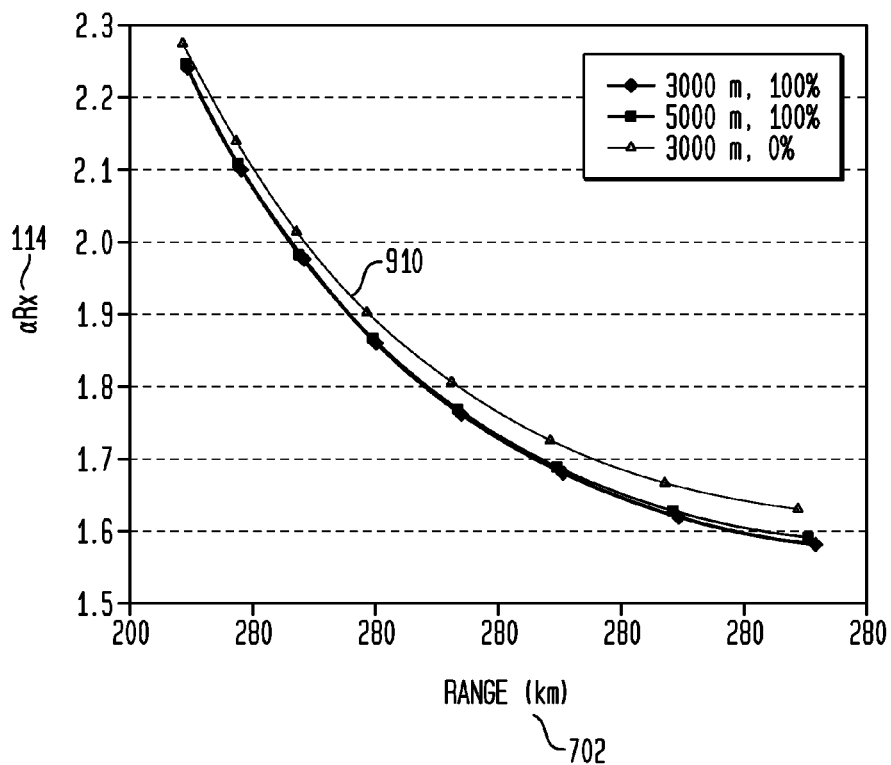
FIG. 9 is a graph of the arrival angle and the range of the horizon as imaged at the aircraft for the same three sample sets as FIG. 7.

Referring now to FIGS. 6*a* and 6*b*, in an embodiment the refractivity profiling system 100 further comprises an estimate of refractivity correlated with altitude. In FIGS. 6*a* and 6*b*, the atmosphere of the Earth 110 is shown as having three layers or altitudes 602*a*, 602*b*, 602*c*. A light path 604*a*, 604*b*, 604*c* connects a visually observable object 606 (indicated by the arrow) with an aircraft 102*a* at the top 602*a* of the upper atmosphere layer. The refractivity profile of the left atmosphere 610 is different from the refractivity profile of the right atmosphere 620. In both the left-hand and right-hand figures, FIGS. 6*a* and 6*b*, the light path 604*a*, 604*b*, 604*c* leaves the object at the same angle of departure 116 relative to the local horizontal 112. Note that using the horizon 124 as the object 606 is one way to ensure that the angle of departure 116 is the same in all cases: by definition, when viewing the horizon 124, each camera 104 sees light that left at a departure angle 116 of zero. The light path 604*a*, 604*b*, 604*c* travels the same distance to reach the aircraft 102*a*, 102*b*, 102*c*, i.e., distance 3A in the left atmosphere 610 is the same as distance 3B in the right atmosphere 620. The arrival angle 114 relative to local horizontal 112 is slightly greater in the left atmosphere 610. In an embodiment, an estimate of the refractivity versus altitude is estimated given only the arrival angle 114 and departure angles 116 for one object 606 and one camera 104 of one aircraft 102, for example by measuring arrival angle 114 of light from the object 606 at multiple locations along the trajectory of the aircraft 102. The departure angle 116 will typically vary for each observation. Similarly, a single aircraft 102 climbing or descending can make measurements at multiple altitudes. Refer also to FIGS. 8 and 9.

In an embodiment, the angle 114, 116 relative to local horizontal 112 that a particular light path 604*a*, 604*b*, 604*c* exhibits is measured at each of several altitudes by coordinating estimates of several aircraft 102*a*, 102*b*, and 102*c* at each altitude 602*a*, 602*b*, 602*c*. FIG. 6*a* illustrates using multiple aircraft 102*a*, 102*b*, and 102*c* to make measurements at the top of each atmosphere layer or altitude 602*a*, 602*b*, 602*c*. (The aircraft themselves are omitted for clarity.) Gray triangles show the arrival angles 114 measured at each position. In the left atmosphere 610, these additional angle measurements reveal that the lowest layer 602*c* has a strong refractivity gradient (it bends the light strongly), while the middle layer 602*b* and the top layer 602*a* have weak refractivity gradients (very little bending). In the right atmosphere 602, the angle measurements reveal that the lowest layer 602*c* has a weak refractivity gradient, the middle layer 602*b* has a very strong gradient, and the top layer 602*a* has a weak gradient. The angle measurements 114, 116 at multiple altitudes altitude 602*a*, 602*b*, 602*c* can strongly constrain an estimated refractivity profile. Refer also to FIG. 7.

Refractivity Profile Estimation

In an embodiment, a computer 108 receives at least one report of angular distance between a measured horizon and a true horizon, and the altitude and position of the aircraft 102 and the orientation of the camera 104. In another embodiment, a computer 108 receives at least one report of angular distance between two objects 606 with known locations, and the altitude 602 and position of the aircraft 102 and the orientation of the camera 104. The computer 108 uses variational analysis accepted in the meteorology community. A vector, x, contains values of atmospheric properties to be estimated. An example of one property contained in x might be the temperature at 15,000 feet, latitude 30 degrees, longitude 50 degrees east. Another value in x might be the humidity at the same location; another might be temperature at 10,000 feet. The values in x are varied to minimize a cost function given by:

$$J(x) = \tfrac{1}{2}(x-x_b)^T B^{-1}(x-x_b) + \tfrac{1}{2}(Hx-y_0)^T R^{-1}(Hx-y_0) \qquad (2)$$

where J is the cost to be minimized, $x_b$ is a prior estimate of x based on other sensors or models, B is a matrix of weights based on confidence in (and covariance of) various values in $x_b$, H is a "forward model" that transforms a given vector of atmospheric properties into a vector of observable quantities such as arrival angle 114 at various times, $y_0$ is the vector of quantities actually observed, and R is a matrix of weights based on confidence in (and covariance of) various values of $H_x$ and of $y_0$. Note that numerical parameters of the forward model H are computed based on the location of the aircraft 102 and the location of objects 606 used for the angle 114, 116 measurements.

In embodiments, the computer 108 that receives angular offset reports and computes a refractivity profile is a computer 108 that is in the aircraft 102. In embodiments, the computer 108 will be on the ground. For example, the aircraft 102 that make angle measurements in a given region may be aircraft 102 belonging to several different airlines, while the computer 108 that receives and assimilates all those measurements is a government or non-government weather service provider 130 (refer to FIG. 1.)

In an embodiment, the refractivity profiling system 100 displays the refractivity information to the pilot of the aircraft 102. In an embodiment, the refractivity profiling system 100 sends the refractivity profile information to a weather forecasting center or weather service provider 130. In an embodiment, the refractivity profiling system 100 shares the refractivity profile information with other nearby aircraft 102 or systems on the ground. In an embodiment, the refractivity profiling system 100 shares raw or interpreted visual data with nearby aircraft 102 to develop a better indication of local weather. In an embodiment, the data is shared via military communications links, for example Link-16.

Experimental and Simulated Performance

Referring now to FIG. 7, a model of the refractivity profiling system 100 varies the relative humidity of the atmosphere from zero to 100% as a function of altitude 604 and varies the altitude 604 of the camera 104 and aircraft 102. The model defines light path 122 propagating from the horizon 124 to the camera 102, and outputs arrival angle 114, and distance or range 702 traveled.

FIG. 7 illustrates the horizon angle 704 (a modeler's label for arrival angle 114) versus range 702 for a camera 104 at various altitudes from 3000 m 706a, to 10,000 m 706b and for the horizon at sea level. The upper curve 710 is for a case with zero humidity. The lower two curves 712, 714 are for humidity varying between zero and 100% in a sinusoidal pattern (i.e., average humidity is 50%.) In the curve with diamond points 712, the sinusoid has 3 km half-wavelength. In the curve with triangle points 714, the sinusoid has 5 km half-wavelength. The horizon angle 704 for the 0% humidity curve from the 50% curves differs by 0.06 to 0.08 degrees at every altitude 706, and is easily distinguished. It is somewhat harder to visually distinguish the two 50% curves: the curve with triangle points 712 is about 0.015 degrees higher at 3000 meters and for altitudes from 6000 to 8000 meters. The gap narrows to about 0.006 degrees at 4000 meter altitude. This gap is easily measurable by a consumer-grade digital camera with a consumer-grade telephoto lens of about 300 mm focal length. In an embodiment, smaller gaps are measured using sophisticated sub-pixel image analysis algorithms in the computer 104.

FIG. 8 illustrates the departure angle 116 and the arrival angle 114 for an aircraft 102 at 3000 meters, using the same three model atmospheres as in FIG. 7. FIG. 9 illustrates the arrival angle 114 and range for an aircraft at 3000 meters observing objects at sea level. As with FIG. 7, the refractivity measurement for the 0% humidity curve 810, 910 from the two 50% curves 812, 814 and 912, 914 in FIGS. 8 and 9 is easily distinguished. The refractivity measurement for the two 50% curves 812, 814 and 912, 914 is measurable using consumer-grade digital cameras with a similar consumer grade telephoto lens of about 300 mm focal length. In an embodiment, smaller gaps are measured using sophisticated sub-pixel image analysis algorithms in the computer 104.

The embodiments of the invention shown in the drawings and described above are exemplary of numerous embodiments that may be made within the scope of the appended claims. It is contemplated that numerous other configurations of the refractivity profiling system 100 may be created taking advantage of the disclosed approach. It is the applicant's intention that the scope of the patent issuing herefrom will be limited only by the scope of the appended claims.

What is claimed is:

1. A refractivity profiling system, comprising:
   an image capturing device for capturing an image of a visual feature;
   a lens having a focal length adapted to focus an image onto said image capturing device such that a combination of said lens and said image capturing device is adapted to resolve at least 100 microradians of angle;
   an image processor adapted to compare a detected position of said visual feature of said image to an expected position of said visual feature to detect a change in arrival angle caused by atmospheric refraction of air between the refractivity profiling system and said visual feature;
   an inertial navigation device providing an orientation data of the refractivity profiling system relative to said visual feature; and
   a global positioning system data providing a position of the refractivity profiling system relative to said visual feature;
   wherein said image processor is adapted to process said global positioning system data and said orientation data to query a geographic information system source for a location of said visual feature, and wherein said image processor is adapted to compute an expected position of said visual feature.

2. The refractivity profiling system of claim 1, wherein said image processor is adapted to compare said image with an image data from said geographic information system source to detect one of a compression of said visual feature and an inversion of said visual feature.

3. The refractivity profiling system of claim 1, wherein said image processor is adapted to process said one of a compression of said visual feature and an inversion of said visual feature to determine a change in departure angle of a light from said visual feature.

4. The refractivity profiling system of claim 3, wherein said image processor is adapted to process said arrival angle and said departure angle to determine a refractivity profile of a parcel of atmosphere.

5. A method of detecting a refractivity profile of a parcel of atmosphere, comprising:
   capturing an image from a platform having an orientation and a position;
   selecting a feature present in said image;
   computing an expected angular position of said feature in said image;
   comparing an observed angular position of said feature in said image with said expected angular position to derive a change in arrival angle, said change in arrival angle being correlated with the refractivity profile;
   determining a refractivity profile of the parcel of atmosphere from said change in arrival angle; and
   predicting a temperature and humidity of the parcel of atmosphere from said refractivity profile.

6. The method of claim 5, wherein said capturing is performed by an image capturing means adapted to capture angular resolutions of approximately 10 microradians to approximately 100 microradians of said image.

7. The method of claim 5, wherein said feature is a horizon.

8. The method of claim 5, wherein said platform is an aircraft.

9. A method of detecting a refractivity profile of a parcel of atmosphere, comprising:
   capturing an image from a platform having an orientation and a position;
   selecting a feature present in said image;
   computing an expected angular position of said feature in said image;
   comparing an observed angular position of said feature in said image with said expected angular position to derive a change in arrival angle, said change in arrival angle being correlated with the refractivity profile;
   querying a geographic information service for an image data correlating to said feature;
   comparing said image to said image data to determine a change in departure angle of a light from said feature, wherein said comparing measures a change in said feature selected from the group consisting of a compression of said feature, and an inversion of said feature; and
   determining a refractivity profile based at least in part on said change in departure angle.

10. A method of detecting a refractivity profile of a parcel of atmosphere, comprising:
    capturing an image from a platform having an orientation and a position;
    selecting a feature present in said image;
    computing an expected angular position of said feature in said image;

comparing an observed angular position of said feature in said image with said expected angular position to derive a change in arrival angle, said change in arrival angle being correlated with the refractivity profile;
capturing a first image of a first horizon in a first direction;
capturing a second image of a second horizon in a second direction;
correlating said first horizon in said first image with said second horizon in said second image to determine said orientation of said platform.

11. An aircraft with a refractivity profiling system, comprising:
   a CCD camera for capturing an image of a topographical feature, said CCD camera adapted to resolve a change in an arrival angle of said topographical feature caused by an atmospheric refraction of a parcel of atmosphere between said CCD camera and said topographical feature;
   an aircraft adapted to mount said CCD camera;
   a processor in said aircraft adapted to compare a detected angular position of said visual feature of said image to an expected angular position of said topographical feature to determine said change in arrival angle, and wherein said processor is adapted to derive a refractivity profile of said parcel of atmosphere from said change in arrival angle;
   an inertial navigation device providing an orientation data of the aircraft relative to said topographical feature; and
   a global positioning system data providing a position of the aircraft relative to said topographical feature;
   wherein said processor is adapted to process said global positioning system data and said orientation data to query a geographic information system source for a data relating to said topographic feature, said processor is adapted to compute an expected angular position of said topographical feature from said data, and said processor is adapted to compare said expected angular position with an angular position of said topographical feature in said image to determine a change in departure angle of a light from said topographical feature by detecting one of a compression of said topographical feature and an inversion of said topographical feature, and wherein said processor is adapted to derive a refractivity profile of said parcel of atmosphere from said change in departure angle.

12. An aircraft with a refractivity profiling system, comprising:
   a CCD camera for capturing an image of a topographical feature, said CCD camera adapted to resolve a change in an arrival angle of said topographical feature caused by an atmospheric refraction of a parcel of atmosphere between said CCD camera and said topographical feature;
   an aircraft adapted to mount said CCD camera; and
   a processor in said aircraft adapted to compare a detected angular position of said visual feature of said image to an expected angular position of said topographical feature to determine said change in arrival angle, and wherein said processor is adapted to derive a refractivity profile of said parcel of atmosphere from said change in arrival angle; wherein said processor is adapted to predict a temperature and a humidity of the parcel of atmosphere from said refractivity profile; and further comprising
   a display for presenting said temperature and said humidity.

13. An aircraft with a refractivity profiling system, comprising:
   a CCD camera for capturing an image of a topographical feature, said CCD camera adapted to resolve a change in an arrival angle of said topographical feature caused by an atmospheric refraction of a parcel of atmosphere between said CCD camera and said topographical feature;
   an aircraft adapted to mount said CCD camera;
   a processor in said aircraft adapted to compare a detected angular position of said visual feature of said image to an expected angular position of said topographical feature to determine said change in arrival angle, and wherein said processor is adapted to derive a refractivity profile of said parcel of atmosphere from said change in arrival angle;
   a communications link adapted to transmit said position and said refractivity profile; and
   a receiving station adapted to receive a plurality of said refractivity profiles and said positions from a refractivity profiling system, said receiving station adapted to aggregate said plurality of said refractivity profiles and said positions into a refractivity profile correlated with altitude when said refractivity profiles overlap a common area and said positions include different altitudes.

* * * * *